United States Patent
Porteous et al.

(10) Patent No.: US 6,399,029 B1
(45) Date of Patent: *Jun. 4, 2002

(54) CHEMICAL PROCESSING USING A DUAL FEEDER SYSTEM, A SAMPLE PORT ASSEMBLY, AND A FLUID FLOW CONTROL SYSTEM

(75) Inventors: William M. Porteous; John Mathew, both of Amarillo, TX (US)

(73) Assignee: Cabot Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/826,747

(22) Filed: Mar. 24, 1997

(51) Int. Cl.$^7$ ................................. G01N 1/02
(52) U.S. Cl. .................. 422/150; 422/108; 422/165; 422/119; 425/130; 73/863.51; 73/863.52; 73/863.54; 423/449.6
(58) Field of Search ................. 422/165, 150, 422/108–115; 423/449.6, 450, 449.1, 449.3, 449.2; 524/409, 495; 264/102, 649; 106/712; 528/481, 500, 501, 502; 526/65, 66, 329; 73/863.54, 863.85, 864.31

(56) References Cited

U.S. PATENT DOCUMENTS

| | | | | |
|---|---|---|---|---|
| 3,195,958 A | | 7/1965 | Goins .......................... 302/17 |
| 3,457,788 A | | 7/1969 | Miyajima .................... 73/422 |
| 3,608,001 A | * | 9/1971 | Kowalski et al. .......... 264/40.6 |
| 3,927,983 A | * | 12/1975 | Gordon et al. .............. 422/110 |
| 3,946,996 A | | 3/1976 | Gergely ....................... 259/10 |
| 3,963,420 A | * | 6/1976 | Matsumoto et al. ........ 436/175 |
| 4,010,001 A | * | 3/1977 | Dollinger .................... 422/109 |
| 4,162,286 A | * | 7/1979 | Gunnell et al. ............. 264/117 |
| 4,162,287 A | * | 7/1979 | Gunnell et al. ............. 264/117 |
| 4,237,092 A | * | 12/1980 | Lewis .......................... 422/62 |
| 4,247,530 A | * | 1/1981 | Cheng et al. ............... 423/450 |

(List continued on next page.)

FOREIGN PATENT DOCUMENTS

| | | | |
|---|---|---|---|
| GB | 1012291 | 12/1965 | |
| JP | 57057134 | 4/1982 | .......... B65G/65/32 |
| JP | 60086424 | 5/1985 | .......... G01G/13/00 |
| JP | 08285663 | 11/1996 | .......... G01G/13/00 |
| WO | WO 96/18688 | 6/1996 | |
| WO | 96/18696 | 6/1996 | |

OTHER PUBLICATIONS

International Search Report for PCT/US98/05617.
Green, et al., "Processing of High Smoothness Furnace Blacks for Semi–Conducting Shields,".

*Primary Examiner*—Jerry D. Johnson
*Assistant Examiner*—Frederick Varcoe

(57) ABSTRACT

Components of a chemical processing system are disclosed. In particular, a chemical processing system is disclosed which includes a chemical mixing or reacting zone, an inlet to the zone, an outlet to the zone, and a vacuum or fluid flow source located downstream of the outlet. The chemical processing system further includes a device to control the amount of vacuum or fluid flow through the zone. Also disclosed is a continuous feeder system having a first loss-in-weight and a second loss-in-weight feeder and a device for measuring a lower limit of feed in each feeder. There is also a device to activate the second feeder when the lower limit is obtained in the first feeder and a device to deactivate the first feeder when the lower limit is detected in the first feeder. A sample port assembly is also disclosed for obtaining a sample of material flowing through a processing system. The sample port assembly includes a port in the assembly and a sample cup holder adapted to be moved in the port to obtain a sample of material without substantially affecting the fluid pressure or flow within the system. The components of the chemical processing system can be used in processes to make carbon black having attached organic groups.

29 Claims, 6 Drawing Sheets

U.S. PATENT DOCUMENTS

| | | | | |
|---|---|---|---|---|
| 4,259,308 A | * | 3/1981 | Kallenberger et al. | 423/449.1 |
| 4,321,862 A | * | 3/1982 | Steveson, III | 99/468 |
| 4,348,361 A | * | 9/1982 | Johnson | 422/150 |
| 4,547,976 A | | 10/1985 | King | 34/10 |
| 4,555,384 A | * | 11/1985 | Morris et al. | 422/109 |
| 4,584,179 A | * | 4/1986 | Galli | 422/187 |
| 4,587,856 A | * | 5/1986 | Otis | 73/863.51 |
| 4,640,221 A | | 2/1987 | Barbee et al. | 118/689 |
| 4,771,642 A | * | 9/1988 | Parth et al. | 73/863.52 |
| 5,024,952 A | * | 6/1991 | Alsop | 436/177 |
| 5,275,793 A | * | 1/1994 | Johannes et al. | 422/285 |
| 5,554,739 A | | 9/1996 | Belmont | |
| 5,559,169 A | | 9/1996 | Belmont et al. | |
| 5,571,311 A | | 11/1996 | Belmont et al. | |
| 5,575,845 A | * | 11/1996 | Belmont et al. | 106/712 |

* cited by examiner

CHEMICAL PROCESSING USING A DUAL FEEDER SYSTEM, A SAMPLE PORT ASSEMBLY, AND A FLUID FLOW CONTROL SYSTEM

FIELD OF THE INVENTION

The present invention relates to components of a chemical processing system. More particularly, the present invention relates to means for improving the chemical feed, means for improving sample removal from a chemical process in operation, and means for maintaining an acceptable fluid flow or vacuum through a chemical processing operation.

BACKGROUND OF THE INVENTION

In many types of chemical processing, there is a need for the physical process parameters to be substantially maintained. Any significant interruption of these parameters can degrade product quality, decrease efficiency, and have other undesirable effects. For example, in many types of chemical processing, there is a need for a substantially uniform and uninterrupted fluid flow through a mixing or reacting zone, such as a pelletizer. While a uniform and uninterrupted fluid flow needs to be maintained, this presents a problem when it comes to trying to obtain a sample of the product in order to check the quality of the product. Many times, if one attempts to sample the product, this creates an interruption in the fluid flow which can affect the product quality.

In addition, in certain types of chemical processing, there is a need to maintain a continuous metering of chemicals into a mixing or reacting zone. The metering of chemicals, many times, not only has to be continuous, but must also maintain a consistent feed rate. Again, if there is an interruption in the continuous metering of chemical or an interruption in the feed rate, this can lead to poor product quality. Accordingly, there is a need to develop a system which permits the continuous metering of chemicals and which can maintain a substantially consistent feed rate as well.

SUMMARY OF THE INVENTION

It is an objective of the present invention to provide an overall chemical processing system which achieves a substantially uniform and uninterrupted fluid flow through a mixing or reacting zone.

Another feature of the present invention is to provide a means for sampling products from a reacting or mixing zone without the interruption of the fluid flow through the mixing or reacting zone.

A further feature of the present invention is to provide a means for the continuous metering of chemicals while maintaining substantially the same feed rate without interruption.

Additional features and advantages of the present invention will be set forth in part in the description which follows, and in part will be apparent from the description, or may be learned by practice of the present invention. The objectives and other advantages of the present invention will be realized and attained by means of the elements and combinations particularly pointed out in the written description and appended claims.

To achieve these and other advantages and in accordance with the purposes of the present invention, as embodied and broadly described herein, the present invention relates to a chemical processing system which includes a chemical mixing or reacting zone; an inlet to the zone; and an outlet from the zone. The chemical processing system also includes a vacuum or fluid flow source located downstream of the outlet and a means to control the amount of vacuum or fluid flow through the chemical mixing or reacting zone.

The present invention further relates to a sample port assembly for obtaining a sample of material flowing through a processing system. The sample port assembly includes a port in the assembly and a sample cup holder adapted to be moved in the port to obtain a sample of the material without substantially affecting the fluid pressure or flow within the system.

The present invention further relates to a continuous feeder having first and second loss-in-weight feeders and means for measuring a lower limit of feed in each feeder. The continuous feeder system further includes means to activate the second feeder when the lower limit is obtained in the first feeder and means to deactivate the first feeder when the lower limit is detected in the first feeder.

Each of these features can be used together in a chemical processing system or can be used individually in the chemical processing industry.

It is to be understood that both the foregoing general description and the following detailed description are exemplary and explanatory only and are intended to provide further explanation of the present invention, as claimed.

The accompanying figures, which are incorporated in and constitute a part of this specification, illustrate several embodiments of the present invention and together with the description, serve to explain the principles of the present invention.

DETAILED DESCRIPTION OF THE PRESENT INVENTION

Figure 1:
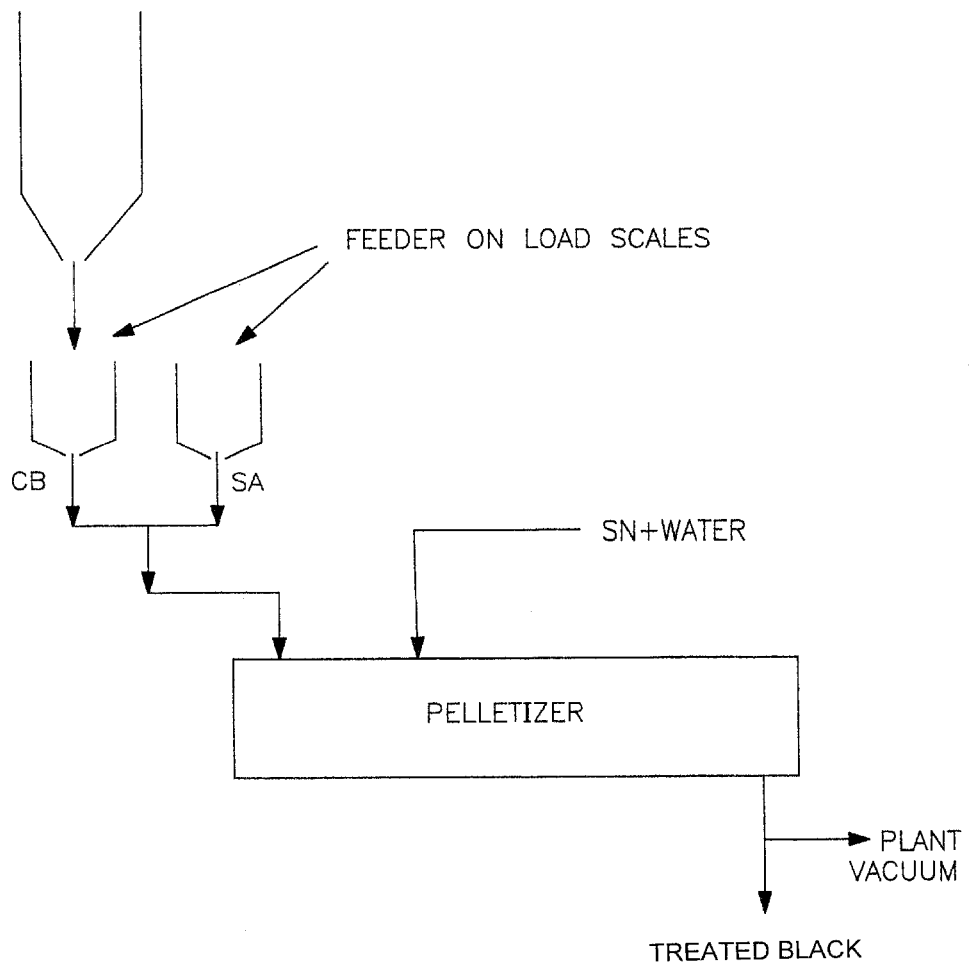
FIG. 1 is a schematic drawing of an embodiment of the present invention representing a process system.

The present invention relates to a chemical processing system which involves the use of a vacuum or fluid flow through a chemical mixing or reacting zone. The fluid flow is generally a gas, such as air. In particular, the chemical processing system includes a chemical mixing or reacting zone and an inlet to the mixing or reacting zone for the entry of one or more chemical components. The processing system further includes an outlet from the chemical mixing or reacting zone for the exiting of one or more chemicals. For purposes of the present invention, the chemical mixing or reacting zone can have more than one inlet and/or more than one outlet. The chemical(s) and the fluid flow or vacuum pass through the inlet, the mixing or reacting zone, and the outlet of the mixing or reacting zone. The fluid flow or vacuum is accomplished by a vacuum or fluid flow source which may be located downstream of the outlet. The processing system also includes means to control the amount of vacuum or fluid flow through the chemical mixing or reacting zone.

The chemical mixing or reacting zone is an area in which one or more chemicals are mixed or reacted with at least one other chemical component. The chemicals that are processed in the chemical processing system of the present invention can be in any state (i.e., a solid, liquid, or gas). An example of a chemical mixing or reacting zone is a pelletizer or pin mixer. A preferred example is a wet pelletizer. The present invention for instance, can be used in the preparation of carbon black pellets having attached organic groups.

In further detail, and only as an example of the preferred embodiment, carbon black and a reactant such as solid sulfanilic acid can be introduced into the inlet of a pelletizer through separate feeders. Once these two components are in the pelletizer, a second reactant, such as a sodium nitrite solution and water can be introduced into the pelletizer through a separate or second inlet. While in the pelletizer, the solid sulfanilic acid and the sodium nitrite solution form a diazonium salt which in turn reacts with the carbon black to form carbon black having attached organic groups. The details of the reaction and the type of organic groups that can be attached to the carbon black are described in detail in U.S. Pat. Nos. 5,554,739; 5,559,169; and 5,571,311; and in U.S. patent applications Ser. Nos. 08/572,336; 081572,525; 08/572,542; and 08/572,545, and PCT Publications Nos. WO/96 18688 and WO/96 18696, all incorporated in their entirety by reference herein.

For example, as described in U.S. Pat. No. 5,554,739, organic groups can be attached to a carbon material selected from a graphite powder, a graphite fiber, a carbon fiber, a carbon cloth, a vitreous carbon product and an activated carbon product.

The carbon black having attached organic groups then exits through an outlet and into a container and optionally on to further processing. Throughout the pelletizer, there is a maintained vacuum or fluid flow (e.g., air flow). The vacuum or fluid flow is created by a blower or other suitable device known to those skilled in the art. This vacuum or fluid flow is created, for instance, by a blower which may be located downstream of the outlet of the mixing or reacting zone. An example of a blower is a regenerative blower, such as an EGG Rotron DR 606 regenerative blower.

In a preferred embodiment of the present invention, the source of the vacuum or fluid flow is located between the outlet of the chemical mixing or reacting zone and the container which receives the treated carbon black. The vacuum or fluid flow source further has means to control the amount of vacuum or fluid flow through the chemical mixing or reacting zone. The vacuum or fluid flow source can have a manual butterfly valve which can be used to manually adjust the vacuum or fluid flow levels. For purposes of the preferred embodiment which makes carbon black having attached organic groups, the vacuum levels should be from about −1.25 mbar gauge to about −0.75 mbar gauge. It is particularly preferred that the amount of vacuum be about 1/10" of vacuum of water.

In making particular chemicals, such as a carbon black having attached organic groups, it is important to maintain a certain vacuum or fluid flow throughout the pelletizer without interruption. Using a vacuum or fluid flow source that has means to control the amount of vacuum or fluid flow permits this control. Generally, the vacuum or fluid flow is controlled by a gauge indicating the amount of vacuum or fluid flow through the chemical processing system and the use of a control system, which is commercially available to maintain the desired fluid flow or vacuum. For instance, the vacuum or fluid flow source can be controlled by a feedback loop between a pressure sensor and a control valve located at the vacuum or fluid flow source. In more detail, the feedback control is used to adjust the manipulated variable of the fluid flow to a desired set point. The manipulated variable could be the pressurelvacuum at the outlet of the mixing or reacting zone. The manipulated variable could also be the pressure/vacuum at the inlet of the mixing or reacting zone or the fluid flow rate through the mixing or reacting zone. The controlling device could be a variable speed fan or a control valve.

Previous operations in making carbon black generally involved discharging the carbon black from a pelletizer into a dryer to remove moisture. The drying of the carbon black would create steam and the emission of the steam, for instance, through a smoke stack, would create a vacuum through the pelletizer. However, such a vacuum was not readily controllable and the emission of such steam could also release contaminants which would create certain environmental concerns. The present invention avoids the emission of steam and the need for a dryer.

Figure 2:
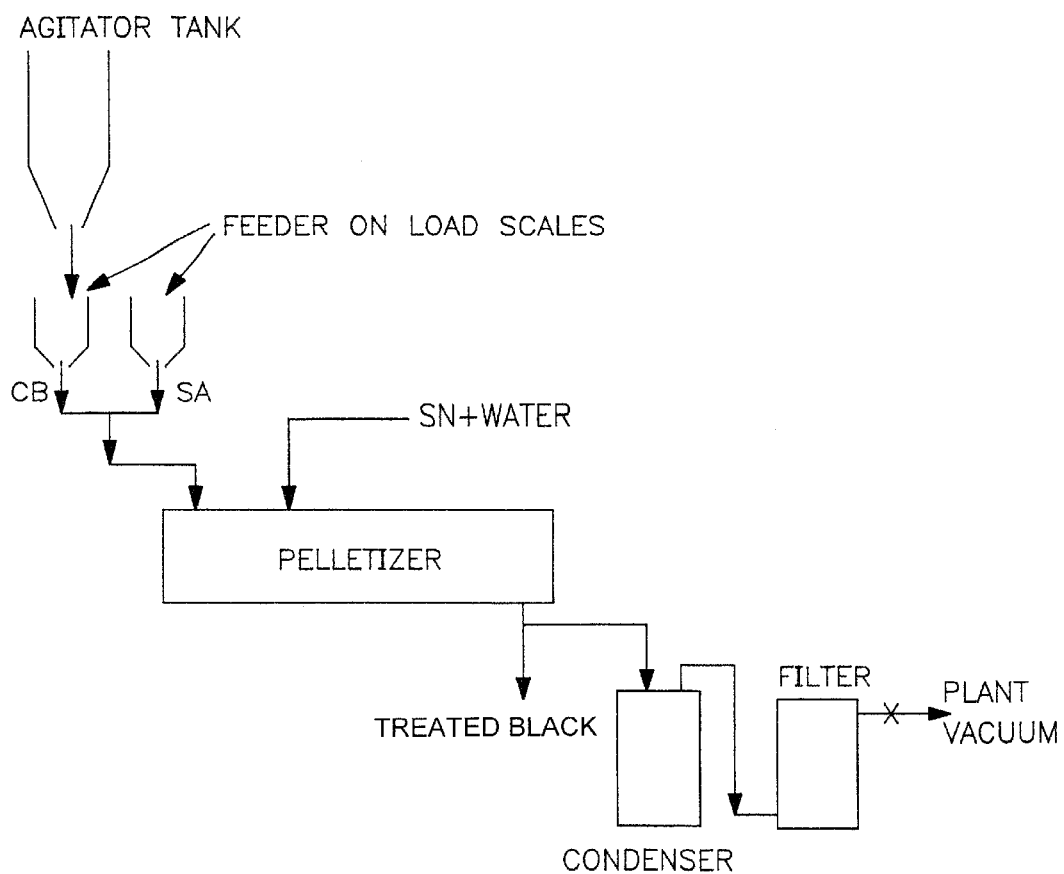
FIG. 2 is also a schematic drawing of an embodiment of the present invention showing a different process system.

In a preferred embodiment, a condenser and/or a filter are located prior to the vacuum or fluid flow source to ensure that moisture is removed from the fluid, such as air, and to also ensure that any chemicals, such as carbon black particles, are substantially removed from the fluid. A schematic of the embodiments showing a processing system with and without condensers and filters are set forth in FIGS. 1 and 2. Though optional, the use of a condenser and/or filter further assists uniform and uninterrupted fluid flow through the pelletizer which permits a consistent and uniform feed and treatment of the chemicals entering the reacting or mixing zone. Commercially available condensers and filters can be used and are familiar to those skilled in the art. For instance, the filter can be bags of standard Pulsaire 4.5 inch diameter bags.

In chemical processing where a vacuum or fluid flow is involved, it is important to ensure that there is no fouling of the vacuum or fluid flow system due to water and/or other chemical accumulations. Such fouling, for instance, with the use of a pelletizer, decreases the fluid flow through the pelletizer. As the fluid flow decreases through the pelletizer, the residence time of the chemicals in the pelletizer correspondingly increases. As residence time increases in the pelletizer, the amount of material within the pelletizer increases and therefore motor load increases. A point is ultimately reached where high levels of treatment and material hold-up causes unwanted and rapid cake formation. The excessive cake accumulations are in turn removed by the pins, resulting in erratic motor loads, severe pelletizer vibration, and poor product quality. It has been discovered that preferably when a condenser and a filter are used, fouling can be even more significantly avoided.

A temperature indicator at the pelletizer's inlet and/or outlet can also be used to monitor the temperature of the reactants and fluid flow through the pelletizer. The temperature indicator can detect rises in temperature which may be an indication of plugging in the pelletizer.

Tables 1 and 2 are representative with respect to a processing system where carbon black having attached organic groups is made and sets forth the various feed rates and pelletizer speeds and temperatures. As can be seen in Table 2, acceptable and consistent flows were obtained throughout the runs using the set up of the present invention.

TABLE 1

Run Conditions

| Run Number | 1 | 2 | 3 | 4 |
|---|---|---|---|---|
| SA/CB (hb) | 12.5 | 12.5 | 12.5 | 12.5 |
| CB Rate (kg/hr) | 45.4 | 45.4 | 45.4 | 45.4 |
| SN/SA mole ratio | 1.1 | 1.1 | 1.1 | 1.1 |
| Total Water and Sodium Nitrite (kg/hr) | 43.1 | 43.1 | 44.0 | 44.0 |
| Pelletizer Jacket Temperature (° C.) | 74 | 74 | 74 | 74 |
| Pelletizer Speed (RPM) | 1000 | 1300 | 1000 | 1150 |

TABLE 2

Accuracies of Chemical Addition Rate

| Run No. | Time* | | 10 Second Basis | | | | 2 Minute basis | | | |
|---|---|---|---|---|---|---|---|---|---|---|
| | | | CB kg/hr | SA kg/hr | Water kg/hr | NaNO$_2$ kg/hr | CB kg/hr | SA kg/hr | Water kg/hr | NaNO$_2$ kg/hr |
| 1 | 9:40 | Set Point | 45.36 | 5.67 | 43.09 | 8.29 | 45.36 | 5.67 | 43.09 | 8.29 |
| | to | MAX | 49.22 | 6.39 | 43.37 | 8.74 | 46.50 | 5.91 | 43.37 | 8.42 |
| | 11:30 | Max dev (%) | 8.50 | 12.63 | 0.65 | 5.43 | 2.52 | 4.31 | 0.64 | 1.59 |
| | | MIN | 41.65 | 5.00 | 42.43 | 7.86 | 44.42 | 5.43 | 42.83 | 8.17 |
| | | Min dev (%)** | 8.18 | 11.76 | 1.55 | 5.20 | 2.07 | 4.21 | 0.60 | 1.44 |
| | | RMS** | 1.25 | 0.22 | 0.12 | 0.13 | 0.38 | 0.09 | 0.11 | 0.04 |
| | | RMS (%)** | 2.75 | 3.81 | 0.29 | 1.57 | 0.83 | 1.62 | 0.27 | 0.46 |
| 2 | 14:40 | Set point | 45.36 | 5.67 | 43.09 | 8.29 | 45.36 | 5.67 | 43.09 | 8.29 |
| | to | MAX | 52.61 | 6.30 | 43.78 | 8.81 | 49.49 | 5.91 | 43.63 | 8.38 |
| | 16:40 | Max dev (%)** | 15.99 | 11.11 | 1.61 | 6.22 | 9.11 | 4.28 | 1.26 | 1.12 |
| | | MIN | 41.68 | 4.81 | 42.31 | 7.88 | 43.80 | 5.32 | 42.83 | 8.21 |
| | | Min dev (%)** | 8.12 | 15.09 | 1.81 | 5.02 | 3.43 | 6.24 | 0.60 | 1.04 |
| | | RMS** | 1.51 | 0.23 | 0.19 | 0.14 | 0.75 | 0.10 | 0.14 | 0.04 |
| | | RMS (%)** | 3.33 | 4.00 | 0.44 | 1.63 | 1.66 | 1.71 | 0.33 | 0.43 |
| 3 | 15:13 | Set point | 45.36 | 5.67 | 44.00 | 8.29 | 45.36 | 5.67 | 44.00 | 8.29 |
| | to | MAX | 49.41 | 6.31 | 44.82 | 8.91 | 47.16 | 5.96 | 44.58 | 8.49 |
| | 17:30 | Max dev (%)** | 8.92 | 11.22 | 1.86 | 7.48 | 3.98 | 5.19 | 1.33 | 2.38 |
| | | MIN | 40.12 | 5.07 | 43.22 | 7.74 | 43.65 | 5.42 | 43.50 | 8.15 |
| | | Min dev (%)** | 11.55 | 10.52 | 1.77 | 6.70 | 3.77 | 4.45 | 1.13 | 1.71 |
| | | RMS** | 1.38 | 0.20 | 0.89 | 0.16 | 0.62 | 0.09 | 0.88 | 0.05 |
| | | RMS (%)** | 3.04 | 3.50 | 2.02 | 1.92 | 1.36 | 1.53 | 2.00 | 0.64 |
| 4 | 13:40 | Set point | 45.36 | 5.67 | 44.00 | 8.29 | 45.36 | 5.67 | 44.00 | 8.29 |
| | to | MAX | 49.37 | 6.41 | 45.84 | 8.72 | 46.93 | 5.91 | 45.12 | 8.51 |
| | 15:40 | Max dev (%)** | 8.83 | 13.04 | 4.19 | 5.21 | 3.46 | 4.24 | 2.54 | 2.69 |
| | | MIN | 41.52 | 5.09 | 42.57 | 7.84 | 43.69 | 5.44 | 43.08 | 8.12 |
| | | Min dev (%)** | 8.47 | 10.31 | 3.24 | 5.41 | 3.68 | 4.05 | 2.08 | 2.12 |
| | | RMS** | 1.33 | 0.22 | 0.98 | 0.15 | 0.62 | 0.08 | 0.94 | 0.05 |
| | | RMS (%)** | 2.92 | 3.80 | 2.22 | 1.79 | 1.37 | 1.47 | 2.13 | 0.65 |

*Time interval over which the statistics were performed. This also corresponds to the time of product collection.
**These are based on deviations from the set point.

In many chemical processing systems, there is a need to sample the material being made to ensure quality control. In systems where a vacuum or fluid flow is present such as the processing system described above, there is a need to create a sample port assembly which does not substantially interrupt the fluid flow or vacuum through the reacting or mixing zone. An additional embodiment of the present invention addresses this need through a sample port assembly which permits the sampling of a product without substantial interruption of the vacuum or fluid flow. A preferred sample port assembly is shown in detail in FIGS. 3–9. The sample port assembly can be located immediately after the outlet of the mixing or reacting zone. A preferred embodiment of the sample port assembly and the sample cup that the sample port assembly can hold is as follows.

Figure 3:
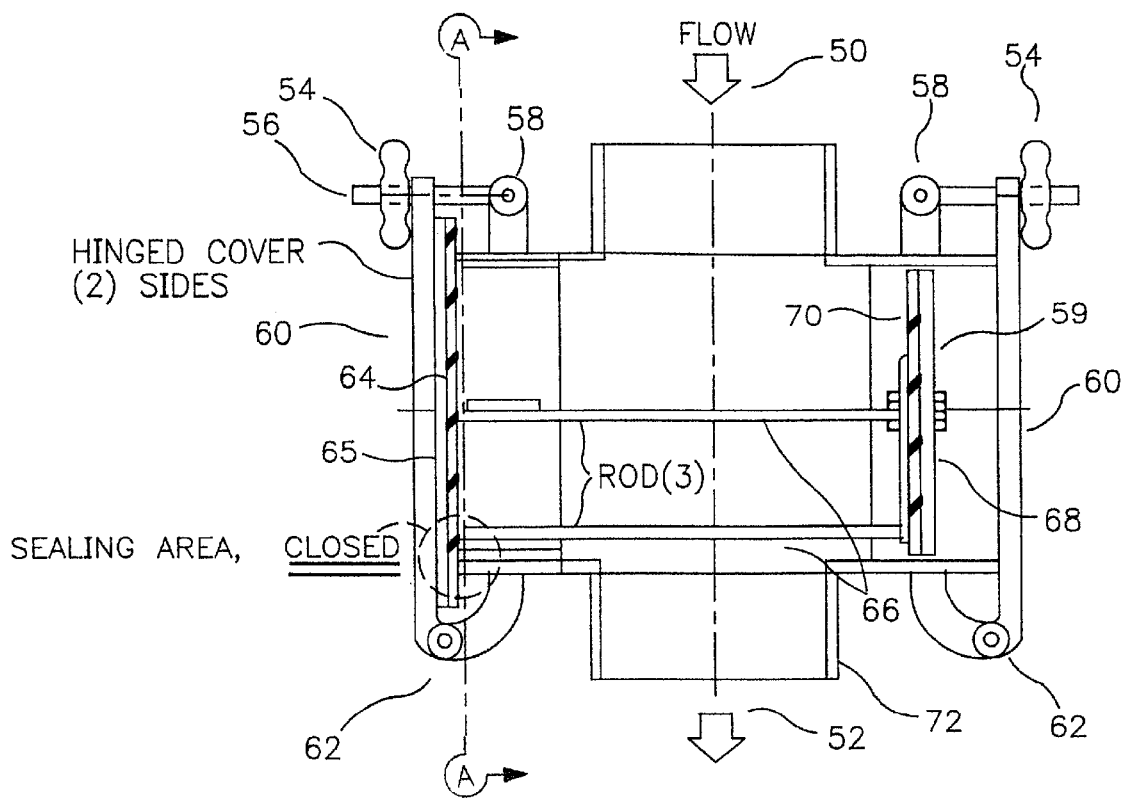
FIG. 3 is a side view of an embodiment of the sample port assembly of the invention, with the cup holder in a closed position.

The sample port assembly illustrated in FIG. 3 comprises a member 72 through which material is transported in the chemical processing system. Member 72 may be a tube or pipe of circular cross section, but should be understood to include any conduit of any suitable cross section through which material is transported in the direction of the arrows from 50 to 52. Member 72 is further configured with an intersecting channel or port adapted to contain a sample cup holder generally designated as 59. The sample port assembly may be constructed of any suitable material that resists degradation by the materials used in the chemical processing system, such as stainless steel.

Sample cup holder 59 comprises at least two elements which form a generally fluid tight seal with the intersecting channel or sampling port to substantially maintain the fluid pressure within the system during operation of the system, and particularly during the sampling procedure. The two elements illustrated in FIG. 3 generally comprise plates 65 and 68 connected by rods 66 in any suitable manner. Although any number of connecting rods may be used, it is preferable to use a minimum number to connect the plates and provide support for the sample cup so that any disruption of the flow of material through member 72 is minimized. Three rods are preferred.

The plates are coated or otherwise contain gaskets 64 and 70 made of any suitable material to create a substantially fluid tight seal with the intersecting channel or sampling port. Any material may be used that will form the required seal, and permit the sample cup holder to slide within the channel or port. A rubber gasket is suitable. It will be noted that plate 65 need not fit within the intersecting channel or port, but may simply abut the port to create the seal.

The sample port assembly of FIG. 3 is further provided with an optional set of hinged cover sides 60 to further assist in maintaining a constant fluid pressure or flow within the system during operation. Cover sides 60 may be secured to the sample port assembly by hinges 62 and to anchors 58 by threaded elements 56 and wing nuts 54. Although the use of hinges permits ready access to the sample cup holder for the sampling process, any suitable means may be utilized to secure the cover sides to the assembly.

Figure 4:
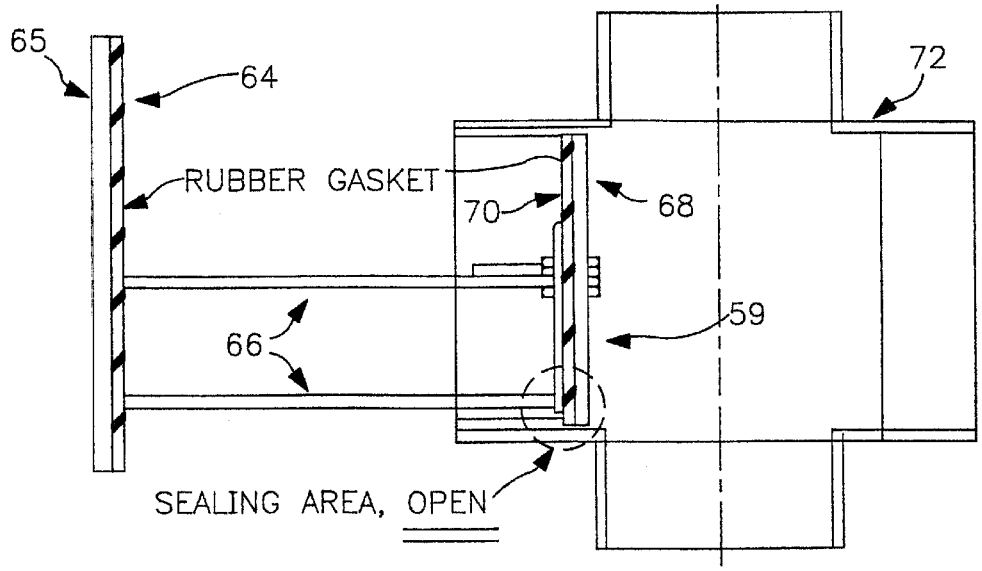
FIG. 4 is a side view of an embodiment of the present invention with the cup holder in an open position to permit insertion of the cup and retrieval of a sample.

FIG. 4 illustrates the cup holder 59 in an open position to permit insertion of the sample cup in the cup holder and retrieval of a sample following the sampling procedure. In the open position, plate 68 and gasket 70 substantially maintain the fluid pressure within the system when the cup is being placed in the cup holder and when the sample is being retrieved.

It should be understood that it is possible to configure the sample port assembly and/or the cup holder 59 in ways to maintain the fluid pressure within the system substantially constant during sampling, or to permit a brief interruption to the uniformity of the fluid pressure within the system. For example, as illustrated in FIG. 4, as the cup holder moves from the closed position to the open position, fluid pressure will not be held constant as plate 68 moves across the flow of material through member 72 unless the flow of fluid, such as a gas like air, through the sampling port is reduced or prevented. This break in fluid pressure could be readily eliminated by, for example, providing another plate within the sampling port or configuring plate 65 to fit securely within the sampling channel until plate 68 reaches the position illustrated in FIG. 4.

Figure 5:
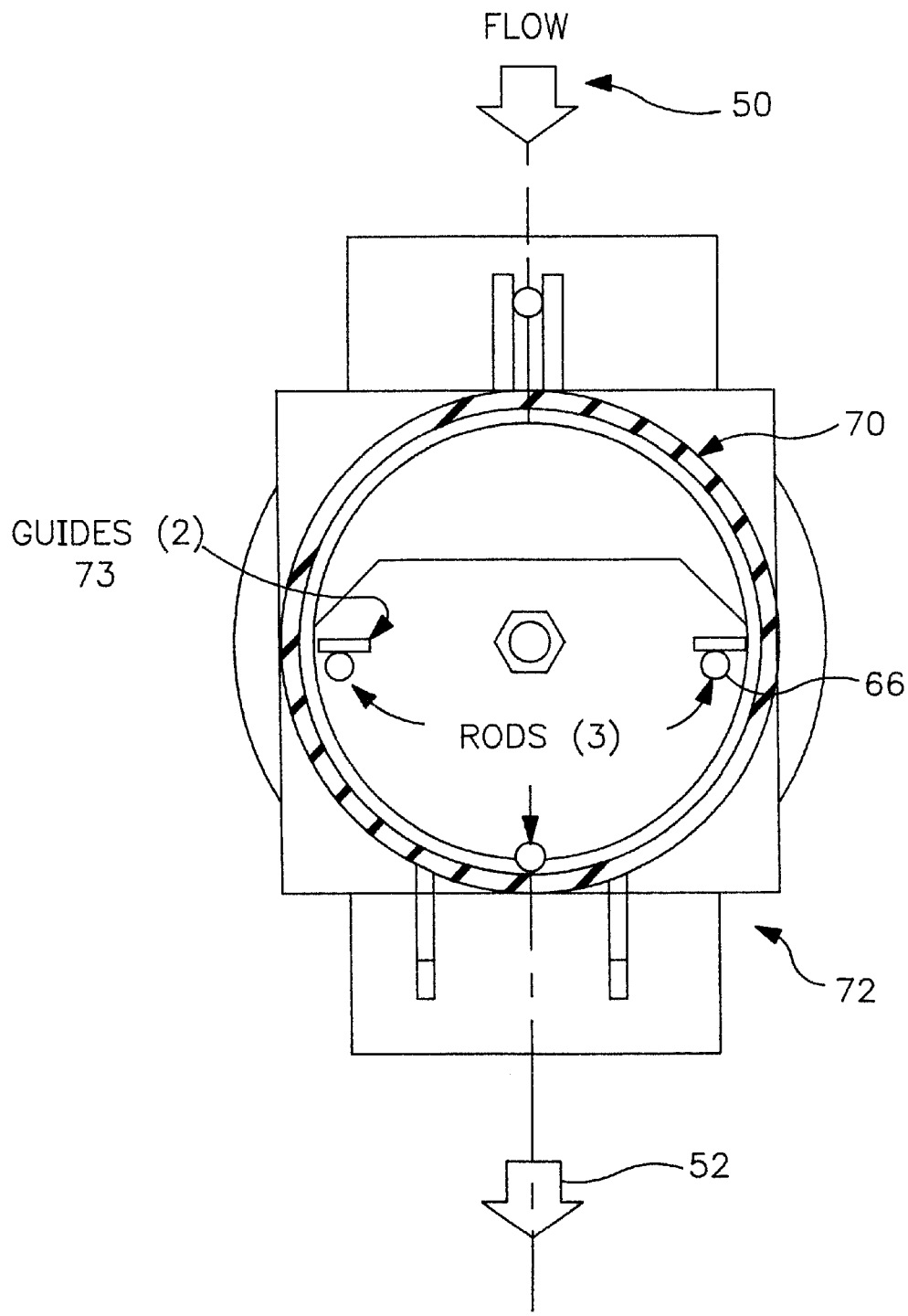
FIG. 5 is a front view of an embodiment of the sample port assembly of a the invention along the line A—A in FIG. 3.

FIG. 5 is a front view of a sample port assembly according to this invention along the line A—A of FIG. 3 illustrating a suitable configuration of the connecting rods 66 which connect the plates that create a substantially fluid tight assembly within the sampling port. The illustrated configuration of the rods provides for a stable connection of the plates and minimum disruption to the flow of material through the assembly. Guides 73 may be provided on member 72 to contact one or more rods of the cup holder.

Figure 6:
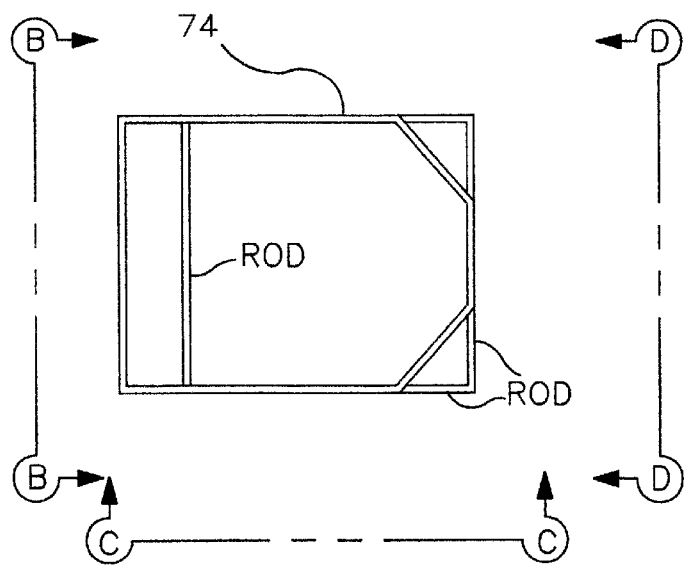
FIG. 6 illustrates a top view of an embodiment of a sample cup according to the present invention.
Figure 7:
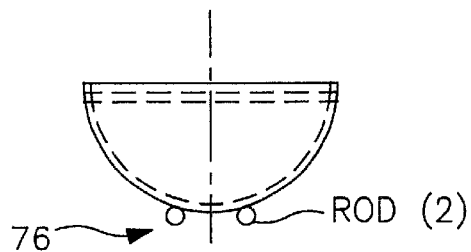
FIGS. 7 and 8 are end views of a sample cup according to one embodiment of the invention taken along the lines B—B and D—D respectively in FIG. 6.
Figure 8:
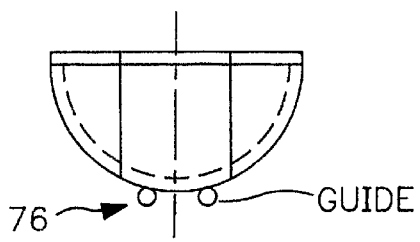
Figure 9:
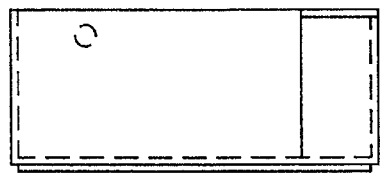
FIG. 9 is a front view of a sample cup illustrated in FIG. 6, taken along the line C—C in FIG. 6.

FIGS. 6–9 illustrate one embodiment of a sample cup within the scope of the present invention. FIG. 6 is a top view of a sample cup 74 having a rectangular shape and comprising several rods to reinforce the sample cup. FIGS. 7 and 8 are end views of a sample cup 74 taken along lines B—B and D—D respectively in FIG. 6. The semicircular shape is merely illustrative because any shape that is sufficient to collect and retain a sample of material would be suitable. Rods 76 are illustrated and can be secured to the cup in any suitable manner and may be used to cooperate with a rod in the cup holder to provide a desired orientation of the cup 74 in the cup holder 59. FIG. 9 is a front view of sample cup 74 taken along line C—C in FIG. 6.

During operation of the processing system, the sample port assembly is maintained in a closed position as illustrated in FIG. 3. When a sample is desired, one of the hinged covers 60 is opened, the sample cup holder 59 is moved to an open position as illustrated in FIG. 4. A sample cup, such as 74 illustrated in FIG. 6, is placed in cup holder 59 in such a way that it will collect a sample of material moving through the sample port assembly 72 when in a closed position. The cup holder is moved to a closed position for a sufficient period of time for an adequate sample to collect in the cup. The cup holder is then moved to an open position to permit removal of the cup and the sample of material. The cup holder is then returned to a closed position without the cup, and the hinged cover returned and secured in a closed position. With the sample port assembly of this invention, the sampling procedure can be accomplished with little or no disruption to the fluid pressure or flow in the system.

The present invention further relates to a system to meter and feed solid chemicals in a continuous manner using dual feeders. In particular, continuous metering of solid chemicals can be essential in the processing industry. Loss-in-weight (LIW) feeders are largely used to accomplish this metering. Currently, the industry generally uses a single loss-in-weight feeder on load cells. The feed rate is estimated based on the weight loss over a period of time. Once the feeder is nearly empty, it is refilled quickly. However, a problem with this set-up is that a true feed rate cannot be measured during the refill operation. During the refill operation, manual or fixed output operation is used in an attempt to maintain an accurate and consistent feed rate. Maintaining an accurate and consistent feed rate during this refilling period is even further complicated when the feed does not have a consistent density, such as with certain types of carbon black.

Figure 10:
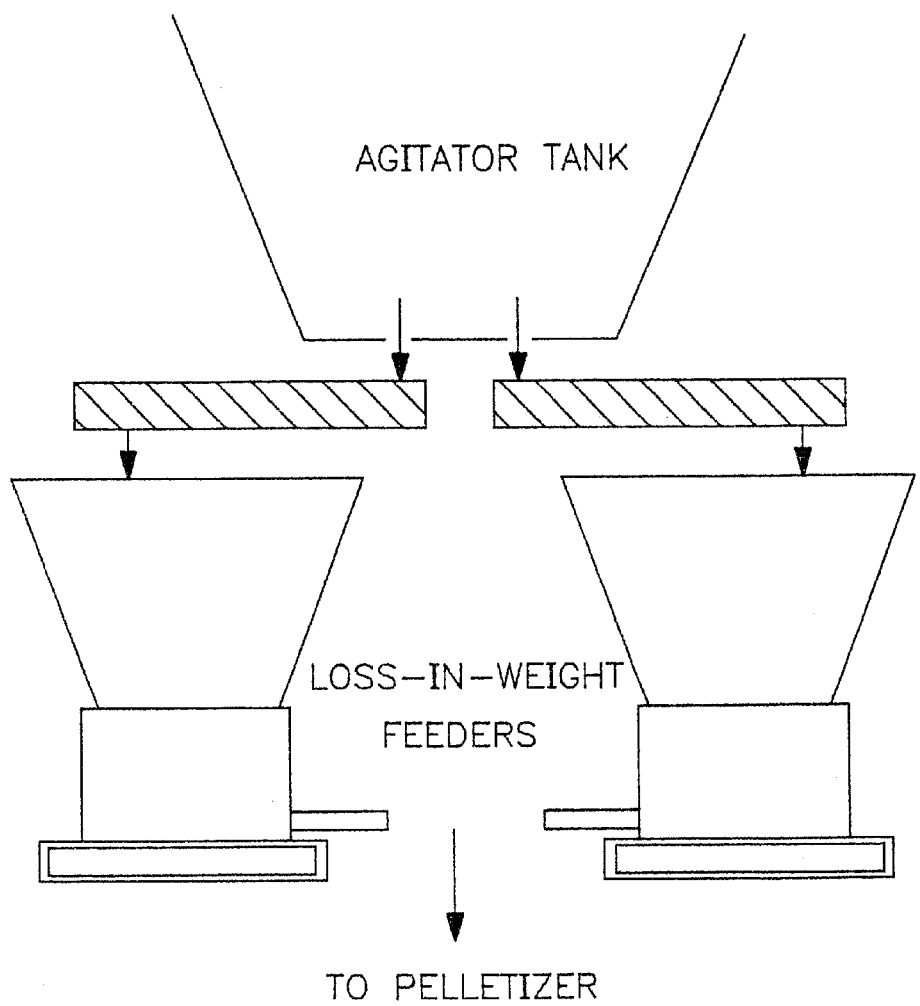
FIG. 10 is a schematic of an embodiment of the present invention showing a continuous dual feeder system.

To avoid this problem, another embodiment of the present invention uses two LIW feeders in sequence. In other words, when the first feeder obtains a preassigned lower weight limit in the hopper, a control gradually switches the feed to the second LIW feeder. Once the control completely switches to the second feeder, the first feeder is then refilled. This switching and refilling is continued for as long as needed. There are a number of ways the switching from the first feeder to the second feeder and vice versa can be performed. One manner is to ramp the set point of each feeder simultaneously. A second way is to ramp the output of one LIW feeder while controlling the other feeder on the total rate. Due to the nonlinear relationship between the screw output and the feed rate, this could involve more sophisticated controls like a feed forward or a fuzzy logic controller. A third way to obtain switching is to switch instantaneously using a diverter valve. A fourth way is to switch instantaneously by turning off one feeder and starting the other at the memorized implied valve position. A loss-in-weight feeder suitable for use in the present invention may be obtained from AccuRate. FIG. 10 sets forth one example of a continuous dual feeder system wherein a solid chemical enters the feeders through an agitator tank.

The present invention will be further clarified by the following examples, which are intended to be purely exemplary of the present invention.

EXAMPLES

A dual LIW feeder system was designed to feed the carbon black to a pelletizer in a continuous mode. The schematic is shown in FIG. 10. Briefly, two high capacity screw feeders were employed to fill two AccuRate feeders (LIW-E and LIW-W) with carbon black from an agitator tank. To achieve optimal overall system performance, a reasonably large hopper capacity and a high rate of refill are preferred, but due to agitator tank to floor plate clearance, hopper volume was 0.524 m$^3$ (18.5 ft$^3$), and the screw feeder to a 0.3 m (12 inch) diameter unit. This combination of equipment resulted in a maximum refill rate of 0.765 m$^3$/min (27 ft$^3$/min), with a corresponding theoretical refill time of 41 seconds. Actual refill time can be less, depending on the angle of repose of the carbon black being processed. Screw feeder specifications were as follows:

Housing 13 in I.D. tubular housing, with 34.5 inch inlet to outlet, 10 gauge, type 316, SS all wetted parts.

Screw: 12 in O.D. sectional screw, 8 inch pitch length, 3/16 inch thick flights, 3" schedule 40S pipe, type 316 SS all wetted parts.

Reducer: Dodge shaft mounted reducer, 25:1 reduction, size no. SCT225, with waste packing seal.

Motor: 3 HP, 1750 RPM, frame 182T, TEFC, 460 Volt, 3 phase, explosion proof, variable speed.

Capacity: 0.765 $m^3$/min (27 $ft^3$/min) at maximum recommended speed of 60 rpm.

The carbon black feed rate was controlled at a fixed rate using a single feeder. When the carbon black in the feeder reached a lower weight limit, the control was gradually switched to the other AccuRate feeder. Once the control was completely switched to the second feeder, the first feeder was refilled. This switching and refilling can be continued until the agitator tank runs out of black.

Experiments at different carbon black rates were performed with various variables such as carbon black type, ramp rate, PID tuning constants, screw, and nozzle. The individual LIW feeders were tuned for each combination of screw, nozzle, and carbon black. The paddle agitator on the LIW-W feeder has a separate drive from that of the screw and this was set at 30% of maximum. This speed was chosen for two reasons: 1) at high agitation speeds, the carbon black may pack in the hopper, and 2) at low speeds, the uneven force on the load cells may not be averaged out.

The appropriate screw and nozzle of the AccuRate feeder can be an important factor in providing a consistent feed of the carbon black. In the case of feeding fluffy carbon black, it was found that for the range of carbon black rates (25–100 kg/hr) investigated, a 3 inch screw with a center rod and a 4 inch nozzle with end discharge gave satisfactory performance. In the case of ground Vulcan 7H carbon black (ground peflets), a modified 3 inch screw with a 3 inch nozzle with end discharge gave uniform feed.

TABLE 3

Run Conditions

| | | | | | West | | | East | |
|---|---|---|---|---|---|---|---|---|---|
| Run No. | Black Grade | Black (kg/hr) | Ramp (kg/hr/sec) | P | I (Rep/Min) | D (Min) | P | I (Rep/Min) | D (Min) |
| 1* | CSX-98 | 23 | 0.23 | 0.15 | 6.8 | 0 | 0.1 | 6.9 | 0.036 |
| 2* | CSX-98 | 23 | 0.09 | 0.15 | 6.9 | 0 | 0.5 | 5 | 0.036 |
| 3* | CSX-98 | 46 | 0.09 | 0.15 | 6.9 | 0 | 0.5 | 5 | 0.036 |
| 4* | CSX-98 | 46 | 0.23 | 0.15 | 6.9 | 0 | 0.5 | 5 | 0.036 |
| 5* | CSX-98 | 46 | 0.23 | 0.3 | 7 | 0.05 | 0.3 | 7 | 0.05 |
| 6* | CSX-98 | 91 | 0.45 | 0.3 | 7 | 0.05 | 0.3 | 7 | 0.05 |
| 7* | CSX-98 | 46 | 0.45 | 0.3 | 7 | 0.05 | 0.3 | 7 | 0.05 |
| 8** | V7H | 46 | 0.45 | 0.15 | 5 | 0.025 | 0.15 | 5 | 0.025 |
| 9** | V7H | 46 | 0.23 | 0.15 | 5 | 0.025 | 0.15 | 5 | 0.025 |

*East feeder used a 3" half pitch screw and a 4" nozzle. West feeder used a 3" standard pitch screw with center rod and a 4" nozzle.
**East feeder used a 3" half pitch screw and a 3" nozzle. West feeder used a 3" standard pitch screw with center rod and a 4" nozzle.

There are a number of ways the switching can be performed. In this trial, a simultaneous ramp of the set points of the two feeders was employed. The sequence was as follows:

1. When the black in the feeder on control hits a lower weight limit, the black rate set point begins a ramp to zero.
2. Simultaneously the other feeder begins ramping from zero to the desired black rate, with the cumulative black rate of both feeders equaling the desired black rate. (The upper and lower weight limits as well as black rate and ramp rate are operator parameters.)
3. Once the switch from one feeder to the other is complete, the "charge" phase begins on the empty feeder which consists of:
   3.1 Starting the high capacity screw
   3.2 Opening the agitator tank slide valve
   3.3 Starting the agitator
   3.4 At this point the weight of the feeder is scanned every two seconds until the high weight limit is reached.
   3.5 Subsequently, the charge equipment is shut down.

The logic was accomplished using two Fisher Provox FSTs (Function Sequence Table).

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A chemical processing system comprising:
   a pelletizer;
   an inlet to said pelletizer;
   an outlet from said pelletizer;
   a source of vacuum or fluid flow located downstream of said outlet;
   means to control an amount of vacuum or fluid flow through said pelletizer; and
   a sample port assembly for obtaining a sample of material flowing through said system, said sample port assembly located between said outlet and said source of vacuum or fluid flow, said assembly comprising a port and a sample cup holder moveable into the port without substantially affecting the vacuum or fluid flow within the system, wherein said sample cup holder has end plates that provide a substantially fluid tight seal in said port and a plurality of rods connecting said end plates.
2. The chemical processing system of claim 1, wherein said source is a gas flow source.

3. The chemical processing system of claim 2, wherein said source is an air flow source.

4. The chemical processing system of claim 3, wherein carbon black and sulfonic acid enter through a first inlet to said pelletizer and sodium nitrite solution and water enter through a second inlet to said pelletizer and a carbon black having an attached organic group exits said outlet.

5. The chemical processing system of claim 1, further comprising a condenser located between said outlet and said source of vacuum or fluid flow.

6. The chemical processing system of claim 1, further comprising a filter located between said outlet and said source of vacuum or fluid flow.

7. The chemical processing system of claim 1, further comprising a condenser and a filter located between said outlet and said source of vacuum or fluid flow.

8. The chemical processing system of claim 1, wherein said pelletizer is a wet pelletizer.

9. The chemical processing system of claim 1, wherein at least one feeder is located before said inlet.

10. The chemical processing system of claim 1, wherein said means to control the amount of vacuum or fluid flow through said pelletizer is a variable speed fan or a control valve.

11. The chemical processing system of claim 1, further comprising a feedback control located before said inlet or after said outlet and which measures the amount of vacuum or fluid flow.

12. The chemical processing system of claim 1, wherein said source of vacuum or fluid flow is a blower.

13. The chemical processing system of claim 12, wherein said blower is a regenerative blower.

14. The chemical processing system of claim 1, wherein said source of vacuum or fluid flow is controlled by a feedback loop between a pressure sensor located at said outlet and a control valve located between said outlet and said source of vacuum or fluid flow.

15. A chemical processing system comprising:
   a chemical mixing or reacting zone;
   an inlet to said zone;
   an outlet from said zone;
   a source of vacuum or fluid flow located downstream of said outlet;
   a condenser located between said outlet and said source of vacuum or fluid flow;
   a control device to control an amount of vacuum or fluid flow through said zone; and
   a sample port assembly for obtaining a sample of material flowing through said system, said sample port assembly located between said outlet and said source of vacuum or fluid flow, said assembly comprising a port and a sample cup holder moveable into the port without substantially affecting the vacuum or fluid flow within the system, wherein said sample cup holder has end plates that provide a substantially fluid tight seal in said port and a plurality of rods connecting said end plates.

16. The chemical processing system of claim 15, further comprising a filter located between said condenser and said source of vacuum or fluid flow.

17. The chemical processing system of claim 15, wherein said source of vacuum or fluid flow is a gas flow source.

18. The chemical processing system of claim 17, wherein said source of vacuum or fluid flow is an air flow source.

19. The chemical processing system of claim 18, wherein carbon black and sulfonic acid enter through a first inlet to said zone and sodium nitrite solution and water enter through a second inlet to said zone and a carbon black having an attached organic group exits said outlet.

20. The chemical processing system of claim 15, wherein said chemical mixing or reacting zone is a pelletizer.

21. The chemical processing system of claim 20, wherein said pelletizer is a wet pelletizer.

22. The chemical processing system of claim 15, wherein at least one feeder is located before said inlet.

23. The chemical processing system of claim 15, wherein said control device is a variable speed fan or a control valve.

24. The chemical processing system of claim 15 further comprising a feedback control located before said inlet or after said outlet and which measures the amount of vacuum or fluid flow.

25. The chemical processing system of claim 15, wherein said vacuum or fluid flow source is a blower.

26. The chemical processing system of claimed 25, wherein said blower is a regenerative blower.

27. The chemical processing system of claim 15, wherein said vacuum or fluid flow source is controlled by a feedback loop between a pressure sensor located at said outlet and a control valve located between said outlet and said vacuum or fluid flow source.

28. The chemical processing system of claim 1, wherein the end plates are provided with a rubber gasket.

29. The chemical processing system of claim 15, wherein the end plates are provided with a rubber gasket.

* * * * *